(12) United States Patent
Wu et al.

(10) Patent No.: US 11,623,349 B2
(45) Date of Patent: Apr. 11, 2023

(54) SYSTEMS AND METHODS FOR GAS DETECTION WITHIN VEHICLES

(71) Applicant: Ford Global Technologies, LLC, Dearborn, MI (US)

(72) Inventors: Bo Wu, Northville, MI (US); Perry Robinson MacNeille, Lathrup Village, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 357 days.

(21) Appl. No.: 17/082,181

(22) Filed: Oct. 28, 2020

(65) Prior Publication Data

US 2022/0126457 A1    Apr. 28, 2022

(51) Int. Cl.
*G01N 33/00* (2006.01)
*B25J 13/08* (2006.01)
*B25J 9/16* (2006.01)
*B25J 11/00* (2006.01)

(52) U.S. Cl.
CPC .......... *B25J 13/087* (2013.01); *B25J 9/1674* (2013.01); *B25J 11/008* (2013.01); *G01N 33/0031* (2013.01)

(58) Field of Classification Search
CPC ...... B25J 13/087; B25J 9/1674; B25J 11/008; G01N 33/0031
USPC .......................... 700/258; 73/864.31, 864.74
See application file for complete search history.

(56) References Cited

U.S. PATENT DOCUMENTS

| | | | |
|---|---|---|---|
| 2020/0274962 A1* | 8/2020 | Martin | H04W 4/02 |
| 2021/0190745 A1* | 6/2021 | Buckingham | G01N 33/0009 |
| 2021/0310893 A1* | 10/2021 | Li | G01M 3/20 |
| 2021/0398289 A1* | 12/2021 | Schmidt | G06N 3/08 |
| 2022/0274780 A1* | 9/2022 | Byeon | G06K 7/1413 |

FOREIGN PATENT DOCUMENTS

| | | |
|---|---|---|
| CN | 202088956 U | 12/2011 |
| CN | 205263046 U | 5/2016 |
| CN | 105784003 A | 7/2016 |
| CN | 106125737 B | 11/2018 |
| CN | 208599024 U | 3/2019 |

* cited by examiner

*Primary Examiner* — Dalena Tran
(74) *Attorney, Agent, or Firm* — Brandon Hicks; Eversheds Sutherland (US) LLP

(57) ABSTRACT

Systems and methods for gas detection within vehicles are disclosed herein. An example method includes monitoring background gas concentrations in a vehicle using a robot having a gas module having a non-selective sensor and a selective sensor, determining a concern index based on output of the gas module, determining when the concern index exceeds a threshold which indicates presence of a non-atmospheric gas, causing the robot to traverse an operating area when the concern index exceeds the threshold to search for a source of the non-atmospheric gas by measuring gas concentration gradients, classifying the non-atmospheric gas using the selective sensor of the gas module and identifying a location of the source of the non-atmospheric gas in the vehicle based on the gas concentration gradients.

20 Claims, 6 Drawing Sheets

SYSTEMS AND METHODS FOR GAS DETECTION WITHIN VEHICLES

BACKGROUND

Undesirable odors may be present in a vehicle. For example, a vehicle occupant may inadvertently spill or leave behind food or drink in the vehicle. In general, these undesirable odors are caused by the presence of non-atmospheric gases in a vehicle cabin. This has become an emergent problem for driverless vehicles, as well as human-driven vehicles. While air quality sensors have been used in vehicles, there are drawbacks to using vehicle-based sensors. For example, a sensor may be required to sense a large number of gases in the presence of constantly changing background gases. Sensing devices must be robust in the automotive environment, fast-acting, and highly selective. A new class of MEMS (Micro Electrical Mechanical Systems) is reaching commercial markets that promise to have this capability and are cost-effective. However, their responses are slow and their fixed position cannot detect specific information regarding these non-atmospheric gases.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
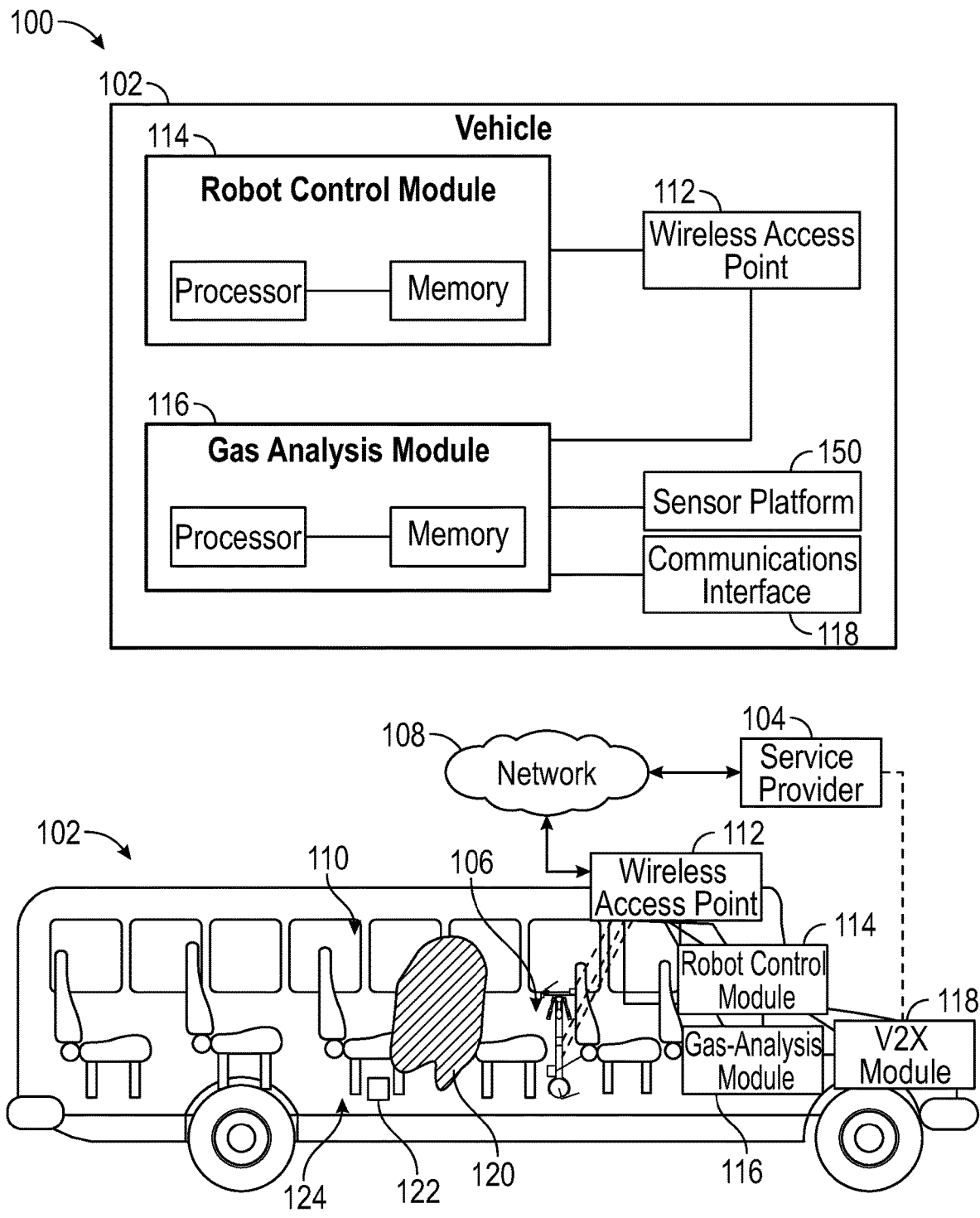
FIG. 1 depicts an illustrative architecture in which techniques and structures for providing the systems and methods disclosed herein may be implemented.
Figure 1:
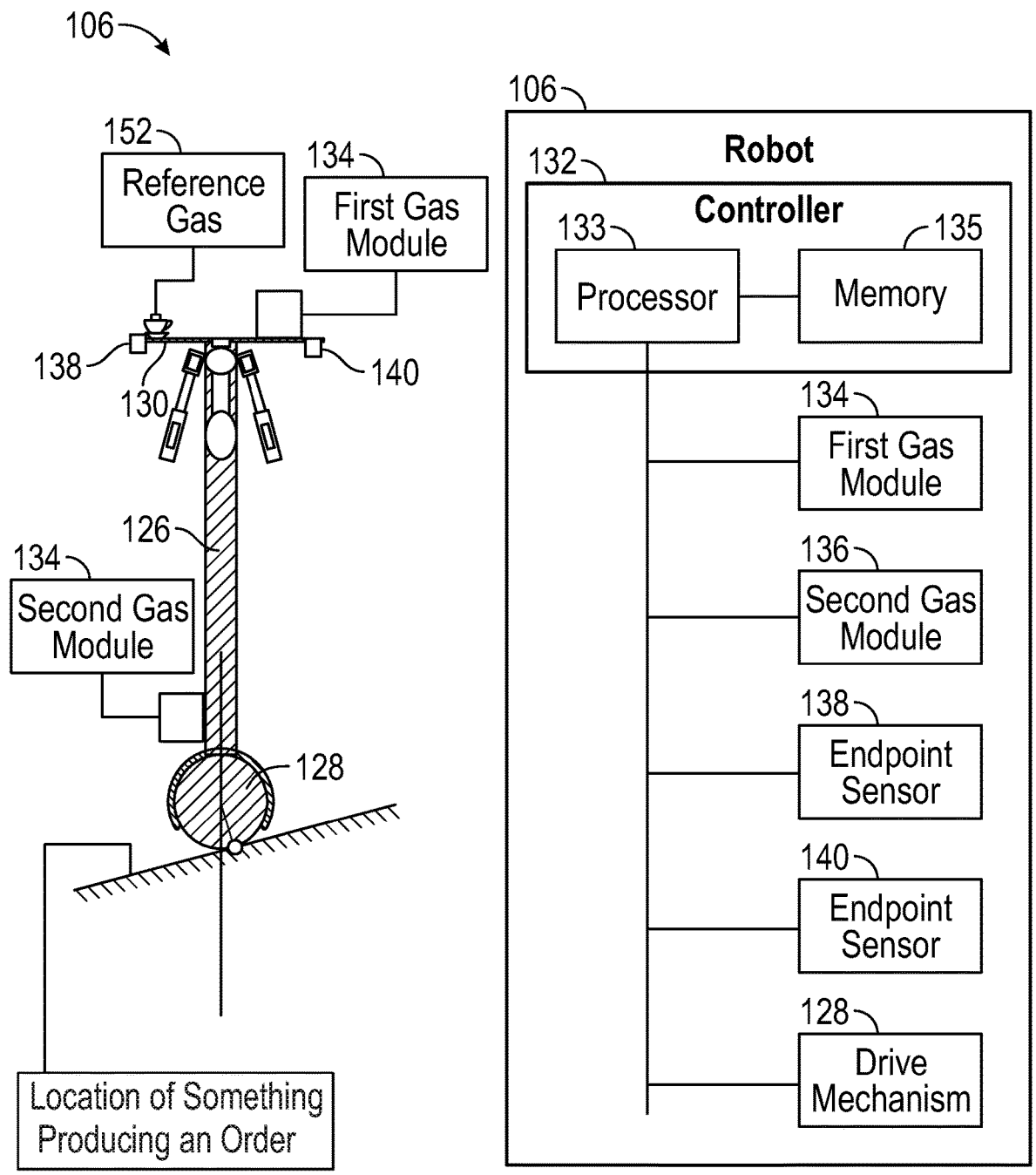

The present disclosure is generally directed to systems and methods that detect the presence of non-atmospheric gases in a vehicle cabin, as well as classifying a type of gas or gases present in the vehicle cabin. A location of a source of the non-atmospheric gases can also be determined. In general, the vehicle can be provisioned with one or more sensor modules that comprise a first gas sensor that is capable of quickly detecting the presence of a non-atmospheric gas, as well as a second gas sensor that is capable of detailed attributes of the non-atmospheric gas that was detected. In some instances, one or more sensor modules can be mounted onto a movable robot. The robot could be a concierge robot that is configured to autonomously operate within a vehicle cabin of the vehicle. Broadly, a non-atmospheric gas can be detected and analyzed using multi-stage sensing and analysis processes as disclosed.

When the presence of a non-atmospheric gas is detected, the robot can be controlled (either autonomously or through remote command) to traverse within the vehicle cabin to determine a source of the non-atmospheric gas in the vehicle cabin. This can be accomplished by using the first gas sensor to detect gas concentration gradients as the robot traverses within the vehicle cabin. The first gas sensor can include any fast-acting, non-selective sensor that generally detects the presence of a non-atmospheric gas. In some instances, the one or more sensor modules can be moved or reoriented on the robot to further refine the gas concentration gradients collected. In general, a non-atmospheric gas can include any gas having a chemical composition with more than two molecules, which can include organic compounds.

Artificial intelligence (AI) can be utilized to determine a set of candidate or possible locations for the source of the non-atmospheric gas. The artificial intelligence can use contextual information such as temperature, air pressure, vehicle HVAC settings, vehicle speed, or other similar information that may affect how gases or fluids may flow through the vehicle cabin. The AI can be configured to iteratively reduce the set of candidate or possible locations to a selected location. This can be accomplished using the contextual information in some instances.

A second gas sensor can be employed that functions as a slow, selective sensor. Output of this sensor can include images that can be processed to classify the non-atmospheric gas based on chemical composition. The use of the second gas sensor can be triggered based on the detected presence of the non-atmospheric gas by the first gas sensor.

In some instances, two or more gas modules can be mounted on an attendant robot inside a vehicle. The gas modules draw in cabin air and analyze the cabin air to determine its chemical composition. An induction point of each of the two or more gas detectors can be moved by the robot. The robot can also move inside the vehicle. Each detector can have multiple stages (such as a first gas sensor and a second gas sensor).

Cabin air can be drawn into a gas module and be rapidly detected using the first gas sensor, allowing for immediate mitigation. A slower but more selective sensor can determine precisely what gas is detected. Sensor positions and outputs can be used as inputs to an AI system. The system also gathers data from vehicle sensors as well. The controller of the robot can use an evidentiary process to move the robot and the induction points of the two or more gas modules to discover the source material and location.

As the evidentiary process continues, a gas analysis module, using the AI logic disclosed herein, can report a set of possible sources to a service provider (such as an autonomous vehicle dispatcher). As the process continues, the AI logic can be used to reduce the number of elements in the set as much as possible. As the size of the set reduces, the service provider can better determine what mitigation approach to use. In some cases, a response from the dispatcher may be rapid even when the set size is large. In other cases, the dispatcher may react slowly, waiting for better knowledge of what sources are detected.

Once a non-atmospheric gas has been detected, a vehicle controller can be configured to mitigate the non-atmospheric gas. Mitigation tactics can include but are not limited to, purging the non-atmospheric gas by opening one or more vehicle windows, dispersing a remediating gas, such as ozone, cleaning of the vehicle, evacuation of vehicle occupant, sealing the vehicle, and extinguishing of a fire—just to name a few.

Illustrative Embodiments

Turning now to the drawings, FIG. 1 depicts an illustrative architecture 100 in which techniques and structures of the present disclosure may be implemented. The architecture 100 can comprise a vehicle 102, a service provider 104, a robot 106, and a network 108. Each of these objects can be communicatively coupled with the network 108. In general, the network 108 includes any private and/or public network that can include short or long-range wireless networks. The vehicle 102 and the service provider 104 can communicate over the network 108 using any suitable vehicle-to-infrastructure (V2I or V2X) communications.

The vehicle 102 can include a vehicle cabin 110 (e.g., operating area), a wireless access point 112, a robot control module 114, a gas analysis module 116, and a communications module (V2X) 118. The robot 106 can operate within the vehicle cabin 110 to detect a non-atmospheric gas 120 in the vehicle cabin 110. Generally, the non-atmospheric gas 120 could emanate from a source 122 within a specific location 124 in the vehicle cabin 110. By way of example, the source 122 could include food left under a seat (specific location 124) of vehicle 102. While detecting a source of a non-atmospheric gas is disclosed as being enabled by the present disclosure, the source may not be inside the vehicle. For example, when the non-atmospheric gas enters the vehicle 102 from an outside source, the non-atmospheric gas can be mitigated or removed as disclosed herein without specifically being required to determine a location of a source of the non-atmospheric gas.

The wireless access point 112 can enable robot-to-vehicle communications over a wireless connection. The robot control module 114 can be used to control robot behaviors such as robot movement in the vehicle cabin 110. The gas analysis module 116 can be configured to detect, classify, and/or remediate a non-atmospheric gas in the vehicle cabin 110. To be sure, some embodiments may reference robot behavior control and/or non-atmospheric gas detection, classification, and/or remediation being performed at the vehicle level (e.g., through the robot control module 114 and the gas analysis module 116). To be sure, these functionalities can be deployed directly at the robot level. In some instances, the robot behavior control and/or non-atmospheric gas detection, classification, and/or remediation features disclosed herein can be performed cooperatively between the robot 106 and the vehicle 102. Thus, when a feature has been described as being performed by the robot control module 114 or the gas analysis module 116 of the vehicle 102, the feature can also be performed at the robot level. Thus, the robot 106 can be configured to collect sensor data, process the sensor data to determine basic or granular information of non-atmospheric gas (including source location), and remediate the non-atmospheric gas.

Generally, the robot 106 can comprise a body 126, a drive mechanism 128, a tray 130, and a controller 132. The body 126 of the robot 106 can have any desired shape or configuration. The drive mechanism 128 can include any drive mechanism that would allow the robot 106 to traverse within the vehicle cabin 110. An example robot that can be configured in accordance with the present disclosure can be found in the co-pending disclosure of U.S. application Ser. No. 16/174,166, filed on Oct. 19, 2018, which is hereby incorporated by reference herein in its entirety, including all references and appendices cited therein. The controller 132 can comprise a processor 133 and memory 135. The memory 135 stores instructions that allow the robot 106 to operate autonomously to sense, analyze, and mitigate non-atmospheric gas. The memory 135 can also store instructions that allow the robot to be controlled by the robot control module 114 of the vehicle 102. Operations disclosed as being enabled by the robot control module 114 and the gas analysis module 116 can be performed at the robot level using the controller 132. Thus, the robot 106 can be configured for autonomous and independent use in non-atmospheric gas detection, processing, and mitigation.

The controller 132 can comprise a processor 133 and memory 135. The processor 133 executes logic stored in the memory 135. In some instances, the controller 132 can include logic that allows the robot 106 to provide concierge services to passengers of the vehicle 102. The controller 132 can be provided with logic that allows the robot 106 to operate within the vehicle cabin 110 to in furtherance of detecting the presence of non-atmospheric gas, as well as the source of the non-atmospheric gas.

The robot 106 can include a first gas module 134 and a second gas module 136. The first gas module 134 and the second gas module 136 can be configured similarly to one another. The first gas module 134 can be disposed on a top portion or end of the robot 106, while the second gas module 136 can be disposed on a lower portion or end of the robot 106. Each of the first gas module 134 and the second gas module 136 can be associated with endpoint sensors, such as endpoint sensors 138 and 140. In some instances, the first gas module 134 and the second gas module 136 can be separated from one another to create spatial diversity. This spatial diversity could be used to determine the attributes of a non-atmospheric gas that may be present in the vehicle cabin 110. For example, some non-atmospheric gases may be heavy and more readily detectable by the second gas module 136, whereas some non-atmospheric gases may be lighter and more readily detectable by the first gas module 134.

In some instances, a position of the first gas module 134 or the second gas module 136 can be adjusted through movement. For example, the robot 106 can be configured to rotate so that the first gas module 134 or the second gas module 136 are sensing for atmospheric gases in a radial pattern. In some instances, the first gas module 134 and/or the second gas module 136 can be configured to move through the use of a track or other similar mechanism associated with the body 126. Generally, movement of the first gas module 134 and/or the second gas module 136 can be used to determine gas concentration gradients as will be discussed in greater detail infra.

Broadly, the robot 106 can move through the vehicle cabin 110 to measure gas concentration gradients. Mapping and measuring gas concentration gradients can help to locate the gas source 122. Comparing gas concentration gradients can be used to determine what gases are present and what the source of the gases is. To be sure, different gases from a single source typically have different gradients.

Figure 2:
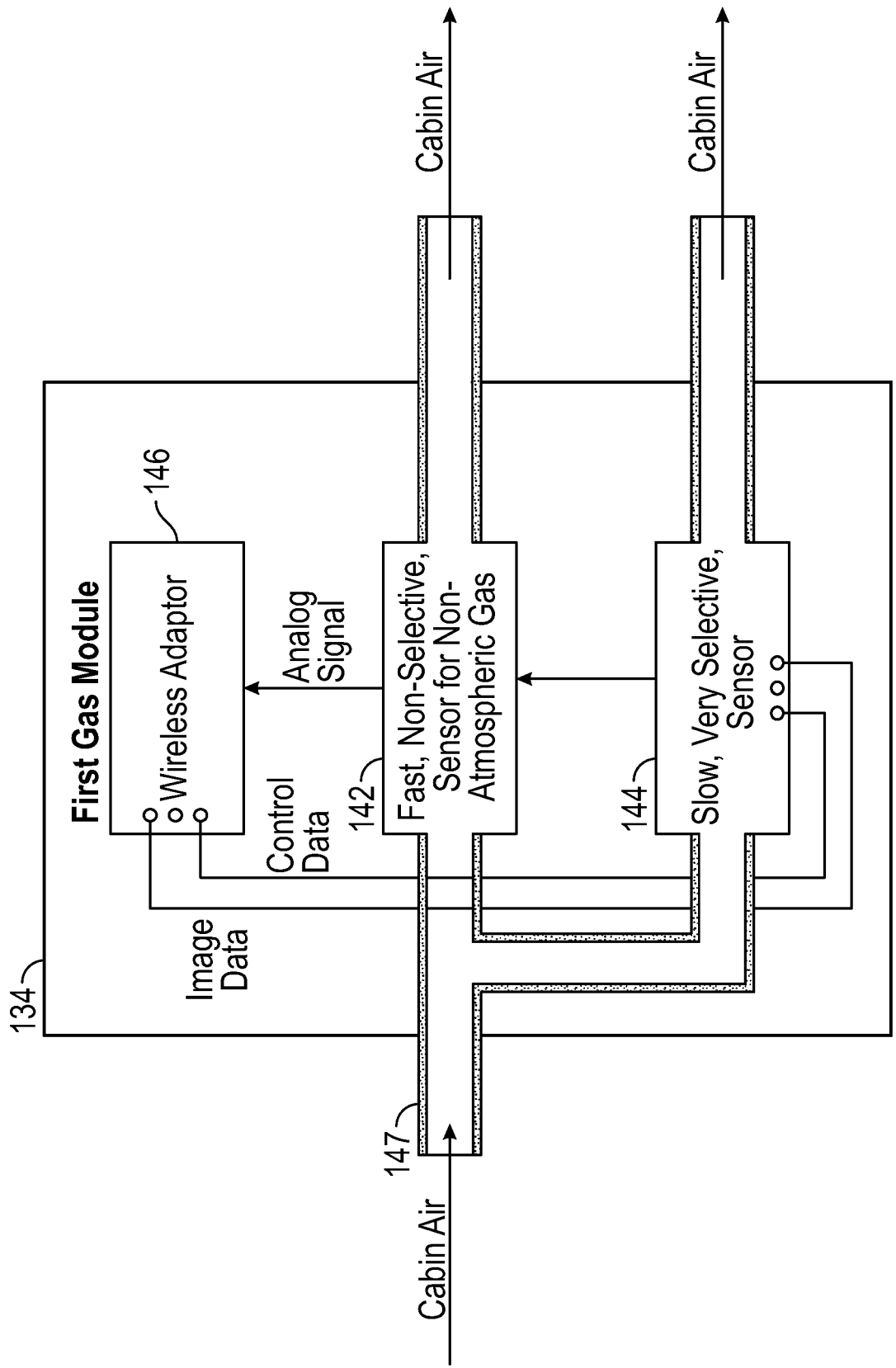
FIG. 2 is a schematic view of an example gas module of the present disclosure having both selective and non-selective gas sensors.

Referring briefly to FIG. 2, a schematic view of the first gas module 134 is illustrated. The first gas module 134 can include a first gas sensor 142, a second gas sensor 144, and a wireless adapter 146. An induction point 147 allows cabin air to enter the first gas module 134. The cabin air can be directed to both the first gas sensor 142 and the second gas sensor 144 for analysis. The first gas sensor 142 can be configured to provide fast, non-selective, sensing of non-atmospheric gases. The first gas sensor 142 can be configured to output an analog signal proportional to a concentration of the non-atmospheric gas. The analog signal can be transmitted to wireless adapter 146. The output of the first gas sensor 142 can be transmitted through the wireless access point 112 to the gas analysis module 116 for processing.

Referring to FIGS. 1 and 2 collectively, once the presence of a non-atmospheric gas is determined by the gas analysis module 116, the robot control module 114 can dispatch instructions to the robot 106 to cause the robot 106 to traverse throughout the vehicle cabin 110 and obtain gas concentration gradients. Generally, the robot control module 114 includes a processor and a memory. The memory stores instructions that allow for control of robot behavior. Likewise, the gas analysis module 116 includes a processor and memory. The memory stores instructions that enable the processing of data output by the gas modules of the robot 106. For example, the analog output and images generated by the gas modules of the robot 106 can be processed by the gas analysis module 116.

These gas concentration gradients are indicative of the relative closeness of the robot 106 to the source 122 of the non-atmospheric gas. In some instances, the first gas sensor 142 can include a photoionization detector or other similar sensor. Any of these features can be used to quickly identify that a non-atmospheric gas is present. Thus, the first gas sensor 142 can be used to monitor background gas concentrations in a vehicle and determine when a non-atmospheric gas is present.

As noted above, the first stage sensor (first gas sensor 142) can include, as an example, a photo-ionization device (PID). Some of the example gases disclosed herein cannot be detected by PIDs. The atmospheric gases are primarily nitrogen, oxygen, argon, carbon-dioxide, neon, helium, methane, krypton, hydrogen, and water vapor. A list of gases a PID sensor cannot detect are: nitrogen, oxygen, carbon-dioxide, sulfur dioxide, carbon monoxide, methane, hydrogen fluoride, hydrogen chloride, fluorine, sulfur hexafluoride and ozone. The PID uses an ultraviolet source with a specific ionization energy. Atmospheric gasses ionize at a higher ionization energy, so these may not be detected. The ionization energy threshold is different in different kinds of PID sensors. CH4, CO2 and CO are special cases requiring a different type of sensor called nondispersive infrared sensor (NDIR) that works on light absorption rather than ionization. Thus in some instances, the first gas sensor 142 can include a PID, a NDIR, or a combination of both PID and NDIR.

Further, once the presence of a non-atmospheric gas is determined, the second gas sensor 144 can be utilized to determine additional details regarding the non-atmospheric gas. For example, the second gas sensor 144 can determine constituent components of the non-atmospheric gas. The second gas sensor 144 can receive the photoionization data of the first gas sensor 142 as input. The gas analysis module 116 can utilize any one or more of high field asymmetric waveform ion mobility spectrometry (FAIMS), gas chromatography-mass spectrometry (GCMS), and/or tunable diode laser absorption spectroscopy (TDLAS)—just to name a few. In some instances, the second gas sensor 144 can output image data to the wireless adapter 146 for transmission through the wireless access point 112 to the gas analysis module 116 for processing. The second gas sensor 144 can also receive control data over the wireless adapter 146 from the gas analysis module 116, such as ionization energy.

As noted above, while this example references the use of the gas analysis module 116 to process data obtained by the first gas sensor 142 and the second gas sensor 144, the analysis methods disclosed can be incorporated into the first gas module 134 using a controller that includes a processor and memory. The memory can include gas analysis logic used to perform the non-selective and/or selective gas analysis methods disclosed herein.

In addition to obtaining data from the first gas sensor 142 and the second gas sensor 144, the gas analysis module 116 can obtain contextual information from a sensor platform 150 of the vehicle 102. The sensor platform 150 can include temperature sensors, barometric pressure sensors, cabin airspeed sensors, vehicle speed, HVAC control settings (e.g., air conditioner or heater operation), and so forth.

In general, factors that influence gas concentration gradients can include but are not limited to, vertical separation between the first gas sensor 142 and the second gas sensor 144 (e.g., gravity segregation). Gas diffusion based on temperature, barometric pressure, molecular collision diameter, concentration gradient, can also influence gas concentration gradients. Convection due to air circulation and mixing can also influence gas concentration gradients. Gas concentration gradients can also be influenced based on gas chemical decomposition, capture, and synthesis.

The gas analysis module 116 can be configured to evaluate the output of the first gas sensor 142 and the second gas sensor 144, along with data obtained from the sensor platform 150 using a context routine. Additionally, the gas analysis module 116 can use behavioral or operational data of the robot 106 as an input. These behavioral or operational data can include robot location, robot speed, robot direction, and the like.

As noted above, the output of the second gas sensor 144 can include images. With respect to processing the data obtained from the second gas sensor 144, the gas analysis module 116 can be configured to process the images. Generally, dimensions of the image data may be limited by the type of sensor used. A range and increment of images can be determined by a control system strategy. For example, a large range can be used to produce a large increment for wide, low-resolution scanning. A small range can be used to produce a small increment for narrow, high-resolution scanning. Boundaries for the images can be shaped as desired and can be irregular. Increments used in processing the images are not necessarily uniform in all instances. Examples of inputs (image dimensions) can include but are not limited to, ionization energy, dispersion field, non-dispersive spectrograph, and ion acceleration field. Example output can include ion current and/or ion energy.

A context routine can be used to create a data store with current context information such as a vehicle location, a location of the robot in the cabin, thermodynamic air measurements, position of the sensors in the vehicle, etc. A history of the image files created can also be created and used in concern index determinations, which are described in greater detail infra. Context location can be obtained from any number of sources such as robot sensors, vehicle sensors, a Smartphone in the vehicle cabin 110, environmental data from the service provider 104, or a navigation database—just to name a few examples.

Figure 3:
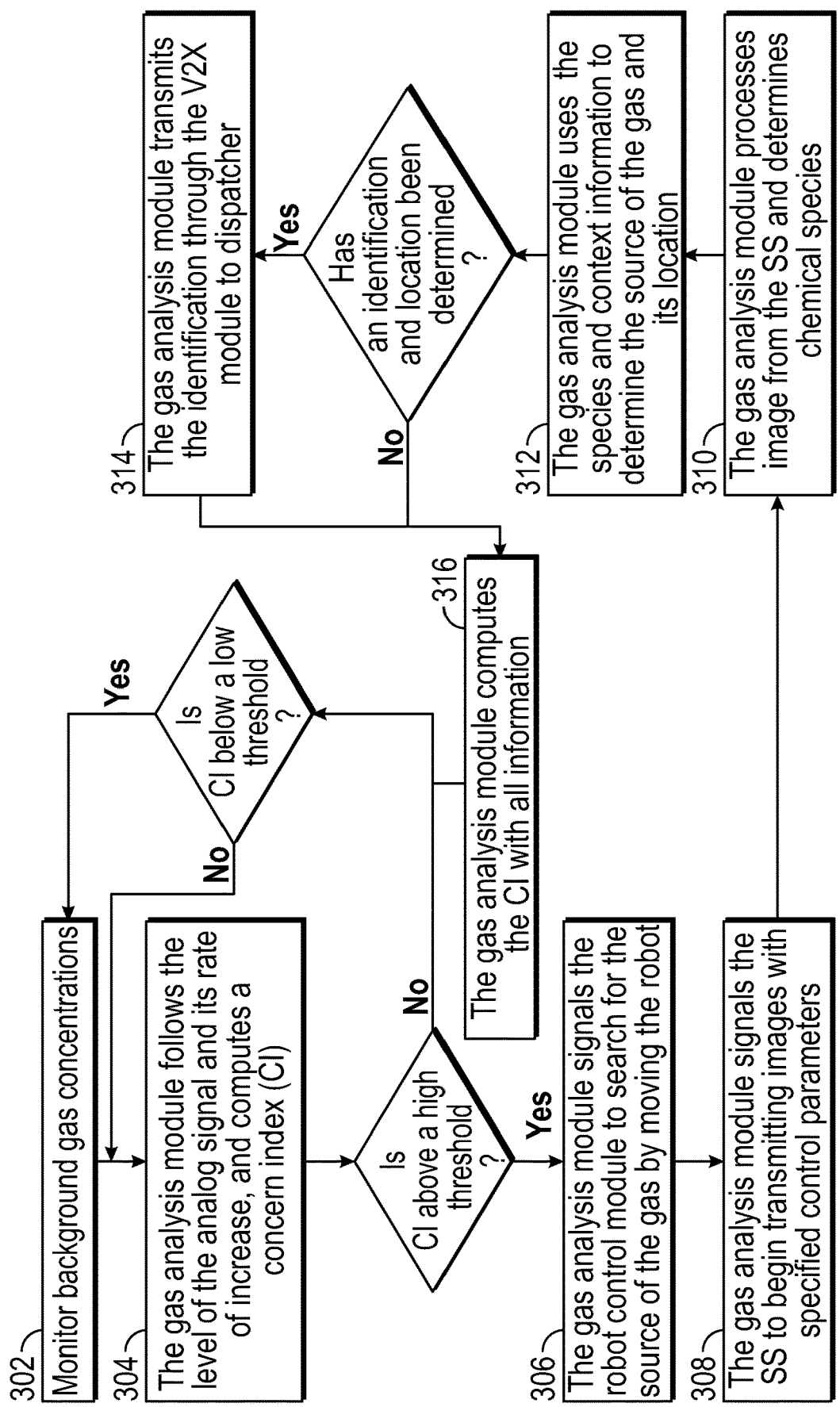
FIG. 3 is a flowchart of an example method of the present disclosure for identifying and locating a source of a non-atmospheric gas in a vehicle cabin using a robot.

FIG. 3 is a flowchart of an example sensor module operational process. The method can include a step 302 of monitoring background gas concentrations using a gas analysis module. The background gas concentrations can be monitored using a plurality of gas modules as described above that can include both selective and non-selective gas sensors. A gas analysis module can be located in the vehicle or in a robot.

The method can include a step 304 of determining if an analog signal generated by a non-selective gas sensor is indicative of the presence of a non-atmospheric gas. This can be determined by determining a rate of increase in a gas concentration gradient. A concern index (CI) can be calculated in some instances that indicate if a non-atmospheric gas is present. If the CI is above a threshold value, the gas analysis module can signal a robot control module to search for a source of the gas analysis module in step 306. This can include moving the robot around the vehicle cabin and detecting changes in gas concentration gradients. As noted above, this can be performed using the first gas sensor that is a non-selective, fast response sensor.

Once the presence of the non-atmospheric gas is determined, the method can include a step 308 where the gas analysis module causes a second gas sensor that is a selective, slower response sensor to collect samples and generate images having specified control parameters. These images are transmitted to the gas analysis module. The gas analysis module can process the images obtained from the second gas sensor to determine an exact (or approximate) chemical species of the non-atmospheric gas in step 310.

In some instances, the gas analysis module can use the species, along with context information to determine a source of the non-atmospheric gas in the vehicle cabin, as well as the source's location in step 312. If the location is determined, the method can include the gas analysis module transmitting the species/type and the location to a service provider in step 314. In some instances, the CI can be recalculated with the collected information, including the species and context information in step 316. Thus, while a general location of the source of the non-atmospheric gas can be determined using the non-selective gas sensor, the CI can be recalculated with additional information that can include the context information and exact species.

Figure 4:
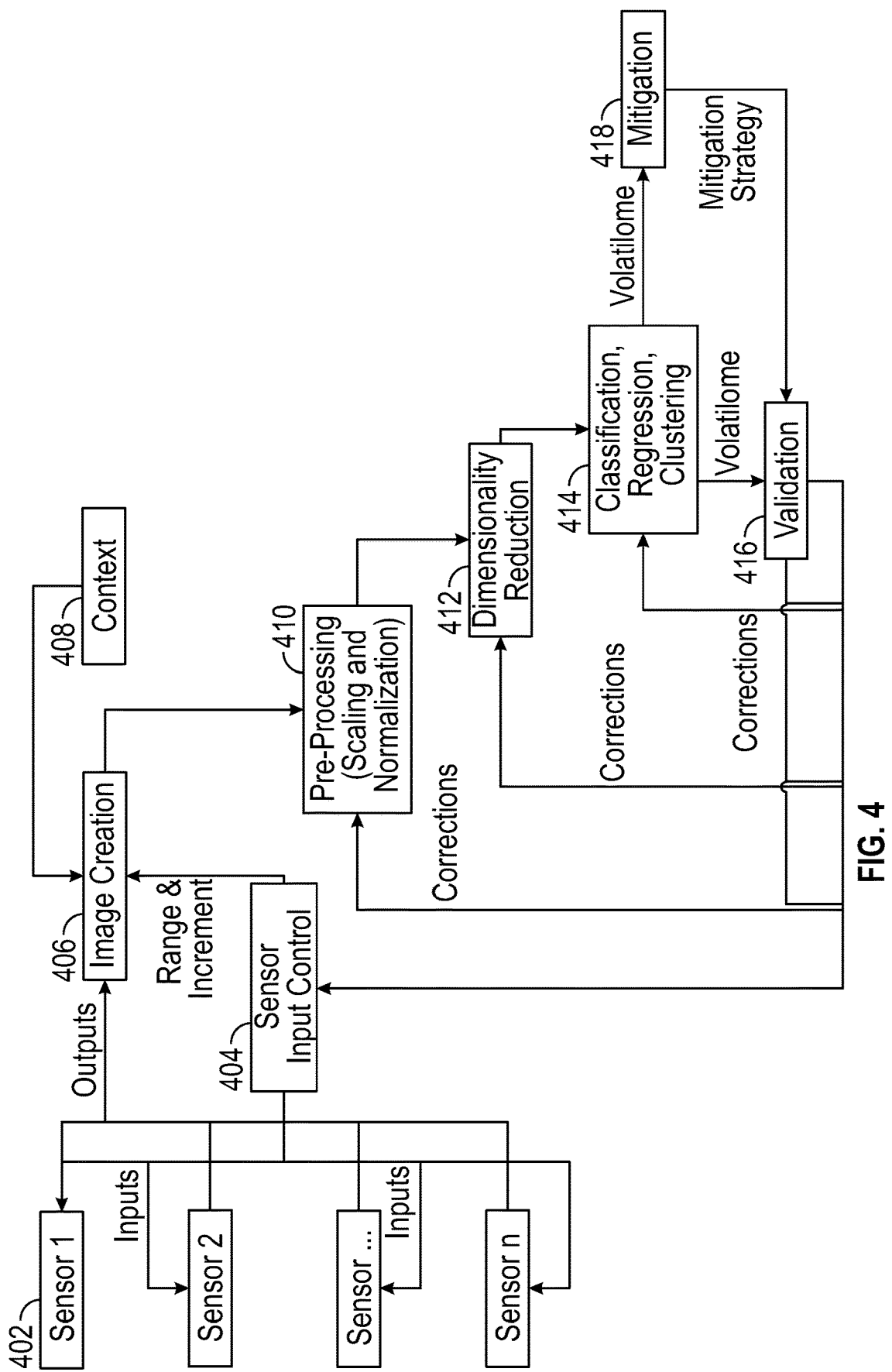
FIG. 4 is a flowchart of another example method of the present disclosure.

FIG. 4 is a schematic flow diagram of an example AI processing and learning system that processes sensor data. While these descriptions reference various components and modules, some may be embodied as logic or applications. A plurality of sensors 402 can be used to obtain sensor data. Example sensor data can be obtained from any of the sensors associated with the robot as described above concerning FIGS. 1-3. The sensor data can also include contextual sensor data obtained from the robot and/or the vehicle that are not specifically related to gas detection. A sensor input control 404 can be used to control input into one or more of the plurality of sensors 402. That is, a particular sensor may utilize input data from another sensor in generating its output. Generally, the output of the plurality of sensors 402 can be directed into an image creation process 406. The images created can be configured based on range and increment data as described above. Context information can be obtained from context sources 408 and incorporated into the image creation process 406.

An image pre-processing process 410 can be used to provide scaling and normalization of image data. A dimensionality reduction process 412 can be used to remove locations within the vehicle cabin where a source of the non-atmospheric gas is not likely to exist. For example, based on concentration gradient data, the dimensionality reduction process 412 can remove areas where concentration gradient data indicate low gas concentration, relative to other locations. The dimensionality reduction process 412 can also consider contextual information. For example, if the non-atmospheric gas is carbon monoxide, the dimensionality reduction process 412 can eliminate locations in the vehicle cabin where carbon monoxide is less likely to be present. Conversely, locations, where carbon monoxide is likely to emanate from, may be selected. Again, these are merely examples and are not intended to be limiting.

A classification, regression, and clustering process 414 can be used to provide a more specific analysis of the non-atmospheric gas. Both artificial intelligence (AI) and non-AI driven approaches can be used. For example, a specific type of non-atmospheric gas can be determined. These analyses can be performed using output from both a first gas sensor and second gas sensor, using both non-specific and specific data.

Once the gas sensor data has been processed, a more complete analysis of non-atmospheric gas can be used to generate volatilome data of the non-atmospheric gas. In some instances, a validation process 416 can be used to create feedback loops and corrective information that can be included back into any of the sensor input control 404, the image pre-processing process 410, the dimensionality reduction process 412, and/or the classification, regression, and clustering process 414. Validation can occur by performing a calibration process. For example, reference gas (see 152 of FIG. 1) can be dispersed by a vehicle system or a robot. In some examples, a volatilome having a predetermined chemical signature can be dispersed by a vehicle system or a robot. The predetermined chemical signature provides a baseline for analysis.

In some instances, a response to the reference gas or volatilome can be determined by the gas analysis module 116 (see FIG. 1 or an equivalent system in the robot). If the response to the reference gas is within an expected range, the performance of the gas analysis module or the sensors used to capture data of the non-atmospheric gas can be verified and/or validated.

In addition to calibration and validation, the gas analysis module can be configured to update or tune the AI logic with feedback. The feedback can be created from data related to prior gas sensing events, or based on the application of a mitigation strategy.

Volatilome data of the non-atmospheric gas can also be used as input to a mitigation process 418. Mitigation can include recirculating cabin-air through a filter of the vehicle, purging cabin air by opening a window of the vehicle, dispersing a neutralizing chemical such as ozone or air freshener, dispersing an adsorbent to bind to the non-atmospheric gas, dispersing a remediating gas, and/or cleaning an interior of the vehicle. A location that requires cleaning can be determined when a source of the non-atmospheric gas is detected based on gas concentration gradient analysis as disclosed above.

Figure 5:
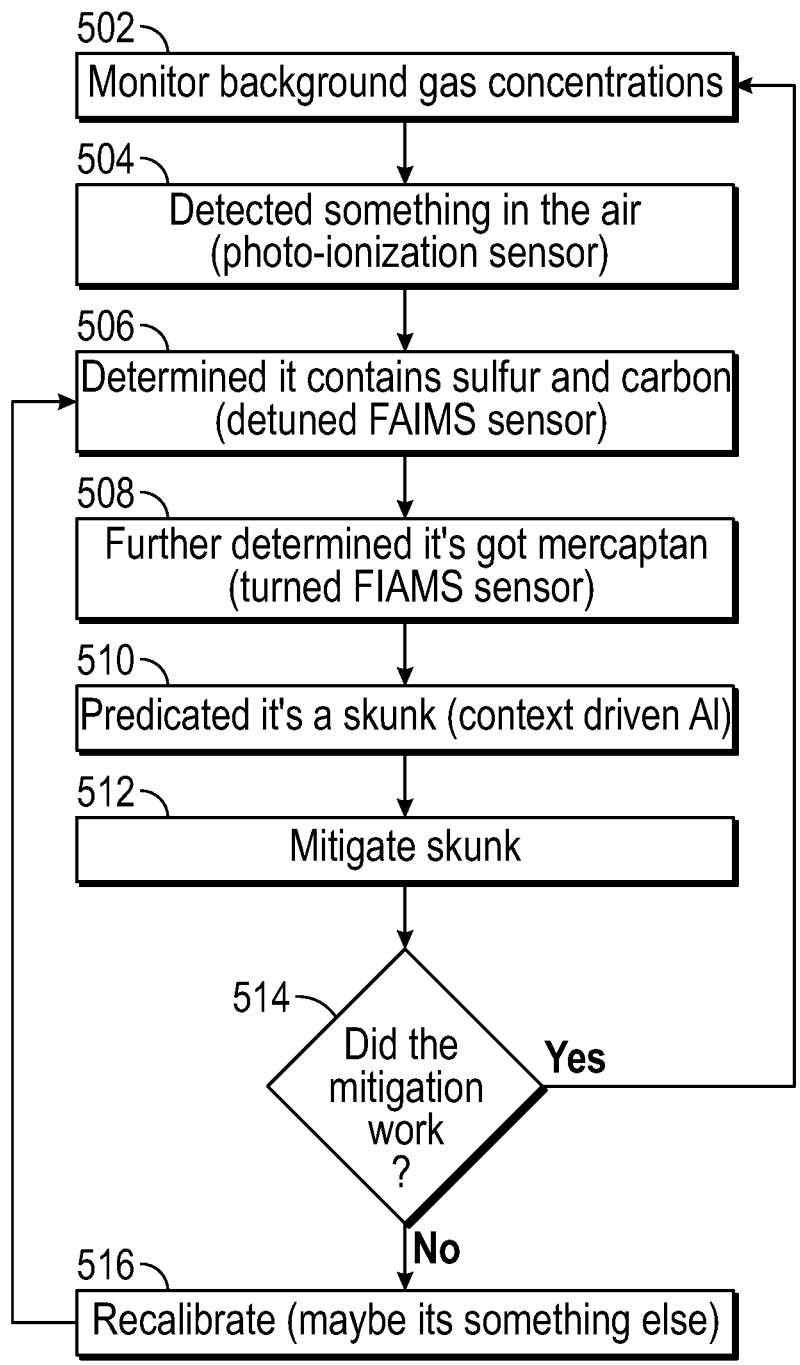
FIG. 5 is a flowchart of an example use case that utilizes the systems and methods disclosed herein.

FIG. 5 is a flowchart of an example use case where detection, analysis, and mitigation of a non-atmospheric gas are disclosed. The method includes a step 502 of monitoring background concentrations of gases inside a vehicle cabin. This can occur using a robot as disclosed above. The robot comprises gas sensors and gas modules that collect the gas data and transmit the same to a gas analysis module. The gas analysis module can reside on the robot, in a vehicle, or at a service provider that is communicatively connected to the robot and/or vehicle. The detection of the non-atmospheric gas can trigger movement of the robot and gas concentration gradient detection, which are described in greater detail above.

In step 504, a first gas sensor detects the presence of a non-atmospheric gas in the cabin air. This could include sensing non-atmospheric gas using a photo-ionization sensor (or other similar sensor(s) disclosed herein) or other similar non-selective, fast-response sensor. In step 506, a second gas module that is selective in its processing can be executed to perform a more detailed analysis of the non-atmospheric gas. Initially, the second gas module detects sulfur and carbon compounds in the non-atmospheric gas. This could be performed by a detuned FAIMS sensor, as an example.

As time progresses, the second gas module can perform additional detailed analysis by tuning the FAIMS sensor, which then detects mercaptan in the non-atmospheric gas in step 508. The tuning of the FAIMS sensor can occur based on contextual data in some instances. For example, in step 510 the AI logic can predict that the non-atmospheric gas includes skunk scent. The method can initiate with sensor signals and progress to a chemical hypothesis, which is indicative of the source.

By way of example, the contextual information could include an onboard vehicle sensor in the vehicle HVAC system sensing an odor in the outside air. Further, as the robot moves, it may detect a particular gas concentration gradient that indicates that the gas is emanating from a vehicle vent. While vehicle sensors have been described, the present disclosure is not so limited. The sensing mechanisms/modules disclosed herein can be implemented and deployed in an Internet-of-Things (IoT) device, a Smartphone, and other similar devices and systems.

In step 512, a mitigation strategy can be used. The mitigation strategy can be tuned to the particularities of the non-atmospheric gas. For example, opening the windows of the vehicle to purge cabin air may not be advantageous as it would draw in additional contaminated air. The mitigation strategy could include the robot dispensing an air freshener. In steps 514 and 516, a determination is made as to whether the mitigation strategy worked or not. This could include performing a reanalysis of cabin air as disclosed above. Specifically in step 516, the sensors may be recalibrated if the mitigation strategy did not work.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," and the like indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, one skilled in the art will recognize such feature, structure, or characteristic in connection with other embodiments whether or not explicitly described.

Implementations of the systems, apparatuses, devices, and methods disclosed herein may comprise or utilize a special purpose or general-purpose computer including computer hardware, such as, for example, one or more processors and system memory, as discussed herein. The processing elements can include a specialized numerical processor such as an array processor for neural networks. Implementations within the scope of the present disclosure may also include physical and other computer-readable media for carrying or storing computer-executable instructions and/or data structures. Such computer-readable media can be any available media that can be accessed by a general-purpose or special-purpose computer system. Computer-readable media that stores computer-executable instructions are computer storage media (devices). Computer-readable media that carry computer-executable instructions is transmission media. Thus, by way of example, and not limitation, implementations of the present disclosure can comprise at least two distinctly different kinds of computer-readable media: computer storage media (devices) and transmission media.

Computer storage media (devices) includes RAM, ROM, EEPROM, CD-ROM, solid-state drives (SSDs) (e.g., based on RAM), flash memory, phase-change memory (PCM), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or any combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description and claims refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein for purposes of illustration and are not intended to be limiting. Embodiments of the present disclosure may be implemented in further types of devices, as would be known to persons skilled in the relevant art(s).

At least some embodiments of the present disclosure have been directed to computer program products comprising such logic (e.g., in the form of software) stored on any computer-usable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

What is claimed is:

1. A robot, comprising:
   a body;
   a drive mechanism associated with the body for translating the robot within an operating area;
   a first gas module disposed on the body; and
   a controller comprising a processor and memory, the processor executing instructions stored in the memory to:
   determine presence of a non-atmospheric gas in the operating area using a non-selective sensor of the first gas module;
   move the robot in an operating area using the drive mechanism to search for a source of the non-atmospheric gas;
   identify a location of the source of the non-atmospheric gas in the operating area; and
   classify the non-atmospheric gas using a selective sensor of the first gas module.

2. The robot according to claim 1, further comprising conducting a mitigating strategy in response to the presence of the non-atmospheric gas.

3. The robot according to claim 1, further comprising a second gas module disposed on an opposing end or an opposing side of the body relative to the first gas module to create spatial diversity between the first gas module and the second gas module, the second gas module also configured with a non-selective sensor and a selective sensor.

4. The robot according to claim 1, wherein the controller is configured to determine a gas concentration gradient as the robot translates within the operating area to identify the location of the source of the non-atmospheric gas.

5. The robot according to claim 1, wherein the first gas module measures any of ionization energy, a dispersion field, a non-dispersive spectrograph, and an ion acceleration field.

6. The robot according to claim 1, wherein the controller is configured to calibrate the first gas module by dispersing a reference gas and measuring a response to the reference gas by the first gas module.

7. The robot according to claim 1, wherein the non-selective sensor is configured to output an analog signal proportional to a concentration of the non-atmospheric gas.

8. The robot according to claim 7, wherein the selective sensor comprises any of high field asymmetric waveform ion mobility spectrometry (FAIMS), gas chromatography—mass spectrometry (GCMS), and tunable diode laser absorption spectroscopy (TDLAS).

9. The robot according to claim 1, wherein the controller is configured to obtain context information that include any of vertical separation between the first gas module and a second gas module that is indicative of gravity segregation, diffusion due to temperature, barometric pressure, molecular collision diameter, concentration gradient, convection due to air circulation and mixing, and chemical decomposition, capture and synthesis.

10. The robot according to claim 1, wherein the controller is configured to cause the first gas module to translate relative to the body to change an induction point of the first gas module.

11. A method, comprising:
    monitoring background gas concentrations in a vehicle using a robot having a gas module comprising a non-selective sensor and a selective sensor;
    determining a concern index based on output of the gas module;
    determining when the concern index exceeds a threshold which indicates presence of a non-atmospheric gas;
    causing the robot to traverse an operating area when the concern index exceeds the threshold to search for a source of the non-atmospheric gas by measuring gas concentration gradients;

classifying the non-atmospheric gas using the selective sensor of the gas module; and identifying a location of the source of the non-atmospheric gas in the vehicle based on the gas concentration gradients.

12. The method according to claim 11, further comprising transmitting the location of the source of the non-atmospheric gas in the vehicle to a service provider.

13. The method according to claim 11, further comprising mitigating the non-atmospheric gas.

14. The method according to claim 13, wherein mitigating the non-atmospheric gas comprises any of:
   recirculating cabin air through a filter of the vehicle;
   purging cabin air;
   dispersing a neutralizing chemical in the operating area;
   dispersing an adsorbent in the operating area;
   dispersing a remediating gas in the operating area;
   cleaning the vehicle;
   evacuation of vehicle occupants;
   sealing the vehicle; and
   extinguishing of a fire.

15. The method according to claim 13, wherein the non-selective sensor processes ionization energy, a dispersion field, and an ion acceleration field to determine the presence of the non-atmospheric gas.

16. A method, comprising:
   detecting presence of a non-atmospheric gas in a vehicle cabin using a first gas module mounted on a robot;
   moving the robot within the vehicle cabin of the vehicle;
   mapping a gas concentration gradient within the vehicle cabin using the first gas module as the robot moves within the vehicle cabin;
   determining a location of a source of the non-atmospheric gas within the vehicle cabin based on the gas concentration gradient; and
   determining a classification for the non-atmospheric gas using a second gas module.

17. The method according to claim 16, wherein determining the location of the source of the non-atmospheric gas within the vehicle cabin comprises:
   moving induction points for the first gas module and the second gas module;
   determining a set of possible locations of the location of the source based on the gas concentration gradient; and
   reducing the set of possible locations to the location using the gas concentration gradient.

18. The method according to claim 16, further comprising calibrating the first gas module or the second gas module by:
   outputting a reference gas or volatilome having a predetermined chemical signature; and
   measuring a response of the first gas module or the second gas module to the reference gas or volatilome.

19. The method according to claim 16, further comprising mitigating the non-atmospheric gas.

20. The method according to claim 19, wherein mitigating the non-atmospheric gas comprises any of:
   recirculating cabin air through a filter of the vehicle;
   purging cabin air;
   dispersing a neutralizing chemical in the vehicle cabin;
   dispersing an adsorbent in the vehicle cabin;
   dispersing a remediating gas in the vehicle cabin; and
   cleaning the vehicle.

* * * * *